United States Patent
Baiazitov

(10) Patent No.: US 10,555,960 B2
(45) Date of Patent: Feb. 11, 2020

(54) USE OF AN AMINOGLYCOSIDE FOR NONSENSE MUTATION SUPPRESSION AND THE TREATMENT OF DISEASE

(71) Applicant: PTC Therapeutics, Inc., South Plainfield, NJ (US)

(72) Inventor: Ramil Y. Baiazitov, East Brunswick, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 15/579,354

(22) PCT Filed: Jun. 3, 2016

(86) PCT No.: PCT/US2016/035709
§ 371 (c)(1),
(2) Date: Dec. 4, 2017

(87) PCT Pub. No.: WO2016/196927
PCT Pub. Date: Dec. 8, 2016

(65) Prior Publication Data
US 2018/0147228 A1 May 31, 2018

Related U.S. Application Data

(60) Provisional application No. 62/171,838, filed on Jun. 5, 2015.

(51) Int. Cl.
*A61K 31/7036* (2006.01)
*A61P 35/00* (2006.01)
*C07H 15/236* (2006.01)
*A61P 43/00* (2006.01)
*A61K 45/06* (2006.01)

(52) U.S. Cl.
CPC .......... *A61K 31/7036* (2013.01); *A61K 45/06* (2013.01); *A61P 35/00* (2018.01); *A61P 43/00* (2018.01); *C07H 15/236* (2013.01)

(58) Field of Classification Search
CPC .... A61K 31/7036; C07H 15/236; A61P 35/00
USPC .......................................................... 514/40
See application file for complete search history.

(56) References Cited

U.S. PATENT DOCUMENTS

| 3,915,955 | A | 10/1975 | Cooper et al. |
| 7,291,461 | B2 | 11/2007 | Welch et al. |
| 2009/0010880 | A1 | 1/2009 | Birk et al. |
| 2009/0093418 | A1* | 4/2009 | Bassov ................ C07H 5/06 514/25 |

FOREIGN PATENT DOCUMENTS

WO    WO 01/44516 A2    6/2001

OTHER PUBLICATIONS

Keeling et al. Suppression of Nonsense Mutations as a Therapeutic Approach to Treat Genetic Diseases. Wiley Interdiscip Rev RNA. Nov. 2011 ; 2(6): 837-852. doi:10.1002/wrna.95. (Year: 2011).*
Adamson et al., 1995, "p53 mutation in the myelodysplastic syndromes." Br J Haematol. 89(1):61-6.
Aji et al., 1997, "L-arginine prevents xanthoma development and inhibits atherosclerosis in LDL receptor knockout mice." Circulation. 95(2):430-7.
Barlow et al., 1999, Loss of the ataxia-telangiectasia gene product causes oxidative damage in target organs Proc Natl Acad Sci U S A. 96(17):9915-9.
Bernhard et al., 2001, "Metabolism of surfactant phosphatidylcholine molecular species in cftr(tm1HGU/tm1HGU) mice compared to MF-1 mice." Exp Lung Res 27(4):349-366.
Bhattacharyya et al., 2001, "A novel missense mutation in lysosomal sulfamidase is the basis of MPS III A in a spontaneous mouse mutant." Glycobiology. 11(1):99-103.
Bhaumik et al., 1999, A mouse model for mucopolysaccharidosis type III A (Sanfilippo syndrome). Glycobiology. 9(12):1389-96.
Bi et al., 1995, "Targeted disruption of the mouse factor VIII gene produces a model of haemophilia A." Nat Genet. 10(1):119-21.
Bluestone et al., 1975, "Chronic experimental hyperuricemic nephropathy." Lab Invest. 33(3):273-9.
Brinkhous et al., 1991, "Willebrand factor and animal models: contributions to gene therapy, thrombotic thrombocytopenic purpura, and coronary artery thrombosis." Mayo Clin Proc. 66(7):733-42.
Brooks et al., 2002, "Functional correction of established central nervous system deficits in an animal model of lysosomal storage disease with feline immunodeficiency virus-based vectors." Proc Natl Acad Sci U S A. 99(9):6216-21.
Bryant et al., 2000, "Development of intermediate-grade (mantle cell) and low-grade (small lymphocytic and marginal zone) human non-Hodgkin's lymphomas xenotransplanted in severe combined immunodeficiency mouse models." Lab Invest. 80(4):557-73.
Burgess et al., 1995, "Evaluation of four animal models of intrarenal calcium deposition and assessment of the influence of dietary supplementation with essential fatty acids on calcification." Urol Res.23(4):239-42.
Bushinsky et al., 1995, "Stone formation in genetic hypercalciuric rats." Kidney Int. 48(6):1705-13.
Bushinsky et al., 1999, "Alendronate decreases urine calcium and supersaturation in genetic hypercalciuric rats." Kidney Int. 55(1):234-43.
Chamberlain and Benian, 2000, "Muscular dystrophy: the worm turns to genetic disease." Curr Biol. 10(21):R795-7.

(Continued)

Primary Examiner — Yih-Horng Shiao
(74) Attorney, Agent, or Firm — Hoffman & Baron, LLP

(57) ABSTRACT

Methods of using and pharmaceutical compositions comprising (2R,3S,4R,5R,6S)-5-amino-6-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-2-(hydroxymethyl)tetrahydro-2H-pyran-3,4-diol are disclosed, including methods of treating or preventing a nonsense mutation mediated disease associated with premature translation termination or a premature stop codon resulting from a germline or somatic nonsense mutation.

10 Claims, No Drawings

(56) References Cited

OTHER PUBLICATIONS

Cichowski et al., 1996, "Nf1 gene targeting: toward models and mechanisms." Semin Cancer Biol. (5):291-8.
Connelly et al., 1998, Sustained phenotypic correction of murine hemophilia A by in vivo gene therapy. Blood. 1;91(9):3273-81.
Connolly et al., 2002, "Complement 3 deficiency and oral prednisolone improve strength and prolong survival of laminin alpha2-deficient mice." J Neuroimmunol., 127(1-2):80-87.
Crawley et al., 1998, Two mutations within a feline mucopolysaccharidosis type VI colony cause three different clinical phenotypes. J. Clin Invest. 101(1):109-19.
Culetto and Sattelle, 2000, "A role for Caenorhabditis elegans in understanding the function and interactions of human disease genes." Hum Mol Genet. 9(6):869-877.
Davidoff et al., 1992, "Expression of p53 in human neuroblastoma-and neuroepithelioma-derived cell lines." Oncogene. 7(1):127-33.
D'Hooge et al., 1999, "Neuromotor alterations and cerebellar deficits in aged arylsulfatase A-deficient transgenic mice." Neurosci Lett. 273(2):93-6.
D'Hooge et al., 1999, "Decline in brainstem auditory-evoked potentials coincides with loss of spiral ganglion cells in arylsulfatase A-deficient mice." Brain Res. 847(2):352-6.
Dove et al., 1995, "Emergent issues in the genetics of intestinal neoplasia." Cancer Surv. 25:335-55.
Dubowitz et al., 2000, "High resolution magnetic resonance imaging of the brain in the dy/dy mouse with merosin-deficient congenital muscular dystrophy." Neuromuscul Disord. 10(4-5):292-298.
Fang et al., 1996, "Lack of persistence of E1-recombinant adenoviral vectors containing a temperature-sensitive E2A mutation in immunocompetent mice and hemophilia B dogs." Gene Ther. 3(3):217-22.
Fantappiè et al., 1992, "Plasma lipoproteins and cholesterol metabolism in Yoshida rats: an animal model of spontaneous hyperlipemia." Life Sci. 50(24):1913-24.
Finkelstein et al., 1998, "Malignant Transformation in Sinonasal Papillomas Is Closely Associated With Aberrant p53 Expression." Mol Diagn. 3(1):37-41.
Fletcher et al., 2001, "Cryptic splicing involving the splice site mutation in the canine model of Duchenne muscular dystrophy." Neuromuscul Disord. 11(3):239-243.
Fodde and Smits, 2001, "Disease model: familial adenomatous polyposis." Trends Mol Med. 7(8):369-73.
Frebourg et al., 1995, "Germ-line p53 mutations in 15 families with Li-Fraumeni syndrome." Am J Hum Genet. 56(3):608-15.
Freedman et al., 2001, "Pancreatic acinar cell dysfunction in CFTR(-/-) mice is associated with impairments in luminal pH and endocytosis." Gastroenterology 121(4):950-957.
Fukutomi et al., 1995, "Familial breast cancer." Nihon Rinsho. 53(11):2764-8.
Fulop et al., 1998, p53, p21, Rb and mdm2 oncoproteins. Expression in normal placenta, partial and complete mole, and choriocarcinoma. J Reprod Med. Feb. 1998;43(2):119-27.
Gallo-Penn et al., 1999, "In vivo evaluation of an adenoviral vector encoding canine factor VIII: high-level, sustained expression in hemophiliac mice." Hum Gene Ther. 10(11):1791-802.
Garinis et al., 2002, "DNA hypermethylation: when tumour suppressor genes go silent." Hum Genet. 111(2):115-27.
Garvey et al., 2002, "The muscular dystrophy with myositis (mdm) mouse mutation disrupts a skeletal muscle-specific domain of titin." Genomics. 79(2):146-149.
Gaschen and Burgunder, 2001, "Changes of skeletal muscle in young dystrophin-deficient cats: a morphological and morphometric study." Acta Neuropathol. 101(6):591-600.
Ghaneh et al., 2001, "Adenovirus-mediated transfer of p53 and p16(INK4a) results in pancreatic cancer regression in vitro and in vivo." Gene Ther. 8(3):199-208.
Grases et al., 1998, "Effects of phytic acid on renal stone formation in rats." Scand J Urol Nephrol. 32(4):261-5.

Grayson et al., 1994, "Novel germline mutation of the p53 tumor suppressor gene in a child with incidentally discovered adrenal cortical carcinoma." Am J Pediatr Hematol Oncol. 16(4):341-7.
Gregory-Evans et al., 2014, "Postnatal manipulation of Pax6 dosage reverses congenital tissue malformation defects." J Clin Invest. 124(1):111-6.
Hanitzsch et al., 1998, Impaired function of bipolar cells in the Royal College of Surgeons rat. Acta Anat (Basel). 162(2-3):119-26.
Harsch et al., 1998, "Effects of pravastatin on cholesterol metabolism of cholesterol-fed heterozygous WHHL rabbits." Br J Pharmacol. 124(2):277-82.
Hasler-Rapacz et al., 1998, "Identification of a mutation in the low density lipoprotein receptor gene associated with recessive familial hypercholesterolemia in swine." Am J Med Genet. 76(5):379-86.
Herber et al., 1996, "Squamous epithelial hyperplasia and carcinoma in mice transgenic for the human papillomavirus type 16 E7 oncogene." J Virol. 70(3):1873-81.
Hill et al., 1991, "Mouse small eye results from mutations in a paired-like homeobox-containing gene." Nature. 354(6354):522-5.
Hino et al., 1999, "TSC2 gene mutant (Eker) rat model of a Mendelian dominantly inherited cancer." Prog Exp Tumor Res. 35:95-108.
Hino O., 2000, "Cancer genetics of TSC2 gene mutant(Eker) rat model". Nihon Rinsho.58(6):1255-61.
Horio et al., 1994, "Predominantly tumor-limited expression of a mutant allele in a Japanese family carrying a germline p53 mutation." Oncogene. 9(4):1231-5.
Hosokawa et al,, 2001, "In vivo analysis of mammary and non-mammary tumorigenesis in MMTV-cyclin D1 transgenic mice deficient in p53." Transgenic Res. 10(5):471-8.
Hough et al., 1998, "A model for spontaneous B-lineage lymphomas in IgHmu-HOX11 transgenic mice." Proc Natl Acad Sci U S A. 95(23):13853-8.
Howes et al., 1994, Photoreceptor cell tumors in transgenic mice. Invest Ophthalmol Vis Sci. 35(2):342-51.
Hsieh et al., 1996, "p53 mutations in gastric cancers from Taiwan." Cancer Lett. 100(1-2):107-13.
Inoue et al., 1986, Effect of DNA-damaging agents on isolated spleen cells and lung fibroblasts from the mouse mutant "wasted," a putative animal model for ataxia-telangiectasia. Cancer Res. 46(8):3979-82.
International Search Report dated Sep. 15, 2016 for PCT Application No. PCT/US16/35709, filed Jun. 3, 2016.
Ishioka et al., 1991, "Mutations of the P53 gene, including an intronic point mutation, in colorectal tumors." Biochem Biophys Res Commun. 177(3):901-6.
Itatani et al., 1979, "Experimental model of calcium-containing renal stone formation in a rabbit." Invest Urol. 17(3):234-40.
Jaissle et al., 2001, "Evaluation of the rhodopsin knockout mouse as a model of pure cone function" Invest Ophthalmol Vis Sci. 42(2):506-13.
Jalanko et al., 1998, "Mice with an aspartylglucosaminuria mutation similar to humans replicate the pathophysiology in patients." Hum Mol Genet. 7(2):265-72.
Jarvis et al., 1996, "Induction of human factor VIII inhibitors in rats by immunization with human recombinant factor VIII: a small animal model for humans with high responder inhibitor phenotype." Thromb Haemost. 75(2):318-25.
Johnson and Bowie, 1992, "Pigs with von Willebrand disease may be resistant to experimental infective endocarditis." J Lab Clin Med. 120(4):553-8.
Jolly et al., 1975, "Bovine mannosidosis—a model lysosomal storage disease." Birth Defects Orig Artic Ser. 11(6):273-8.
Jones et al., 1991, "The evaluation of urinary protein patterns in a stone-forming animal model using two-dimensional polyacrylamide gel electrophoresis." J Urol. 145(4):868-74.
Kado et al., 2001, "Intestinal microflora are necessary for development of spontaneous adenocarcinoma of the large intestine in T-cell receptor beta chain and p53 double-knockout mice." Cancer Res. 61(6):2395-8.
Kajiyama et al., 1998, "p53 gene mutation in 150 dissected lymph nodes in a patient with esophageal cancer." Dis Esophagus. 11(4):279-83.

(56) References Cited

OTHER PUBLICATIONS

Kawamura et al., 1999, "Alterations of the p53, p21, p16, p15 and RAS genes in childhood T-cell acute lymphoblastic leukemia." Leuk Res. 23(2):115-26.
Kay et al., 1994, "In vivo hepatic gene therapy: complete albeit transient correction of factor IX deficiency in hemophilia B dogs." Proc Natl Acad Sci U S A. 91(6):2353-7.
Kloehn et al., 2001, Expression and distribution of the prolactin receptor in normal rat liver and in experimental liver cirrhosis. Horm Metab Res. 33(7):394-401.
Kobayashi et al., 1982, "A highly predictable animal model of retinoblastoma." Acta Neuropathol. 57(2-3):203-8.
Kobayashi et al., 2001, "A germ-line Tsc1 mutation causes tumor development and embryonic lethality that are similar, but not identical to, those caused by Tsc2 mutation in mice." Proc Natl Acad Sci U S A. 98(15):8762-7.
Krämer et al., 1998, "Myotonic ADR-MDX mutant mice show less severe muscular dystrophy than MDX mice." Neuromuscul Disord. Dec. 1998;8(8):542-550.
Kumar et al., 1991, "A new model of nephrolithiasis involving tubular dysfunction/injury." J Urol. 146(5):1384-9.
Kung et al., 2000, "Suppression of tumor growth through disruption of hypoxia-inducible transcription." Nat Med. 6(12):1335-40.
Kuraguchi et al., 2000, "Tumor-associated Apc mutations in Mlh1-/- Apc1638N mice reveal a mutational signature of Mlh1 deficiency." Oncogene. 19(50):5755-63.
Kwiatkowski et al., 2002, "A mouse model of TSC1 reveals sex-dependent lethality from liver hemangiomas, and up-regulation of p70S6 kinase activity in Tsc1 null cells." Hum Mol Genet. 11(5):525-34.
Lai et al., 1980, "Retinitis pigmentosa. Animal model:hereditary retinal degeneration in Wag/Rij rats." Am J Pathol. 98(1):281-4.
Lepelley et al., 1994, "Detection of p53 mutations in hematological malignancies: comparison between immunocytochemistry and DNA analysis." Leukemia. 8(8):1342-9.
Lewis et al., 1998, "A common human beta globin splicing mutation modeled in mice." Blood. 91(6):2152-6.
Li et al., 2000, "Preventing neural tube defects with periconceptional folic acid supplementation: a population-based intervention program in the China." Zhonghua Yi Xue Za Zhi. 80(7):493-8 (Original publication in Chinese with English Abstract only).
Lozier et al., 1999, "The rhesus macaque as an animal model for hemophilia B gene therapy." Blood. 93(6):1875-81.
March et al., 1997, "GABAergic neuroaxonal dystrophy and other cytopathological alterations in feline Niemann-Pick disease type C." Acta Neuropathol. 94(2):164-72.
Masuda et al., 2000, "Mutation analysis of the p53 tumor suppressor gene using paraffin-embedded specimens of human transitional cell carcinomas by the direct sequencing method." Tokai J Exp Clin Med. 25(2):69-77.
Matzner et al., 2002, "Bone marrow stem cell-based gene transfer in a mouse model for metachromatic leukodystrophy: effects on visceral and nervous system disease manifestations." Gene Ther. 9(1):53-63.
Mayers et al., 2013, Regulation of ubiquitin-dependent cargo sorting by multiple endocytic adaptors at the plasma membrane. Proc Natl Acad Sci U S A. Jul. 16, 2013;110(29):11857-62.
McIntyre et al., 1994, Germline mutations of the p53 tumor suppressor gene in children with osteosarcoma. J Clin Oncol. 12(5):925-30.
Mesfin and Breech, 1996, "Heritable nephroblastoma (Wilms' tumor) in the Upjohn Sprague Dawley rat." Lab Anim Sci. 46(3):321-6.
Mizuguchi et al., 2000, "Novel cerebral lesions in the Eker rat model of tuberous sclerosis: cortical tuber and anaplastic ganglioglioma." J Neuropathol Exp Neurol. 59(3):188-96.
Monroy et al., 2002, "Abnormal osteoclast morphology and bone remodeling in a murine model of a lysosomal storage disease." Bone. 30(2):352-9.

Morris et al., 1998, "Lung-specific expression in mice of a dominant negative mutant form of the p53 tumor suppressor protein." J La State Med Soc. 150(4):179-85.
Mount et al., 2002, "Sustained phenotypic correction of hemophilia B dogs with a factor IX null mutation by liver-directed gene therapy." Blood. 99(8):2670-6.
Murphy et al., 1987, "Cell cultures derived from Wilms' tumour animal model." Anticancer Res. 7(4B):717-9.
Nakamura et al., 1992, "p53 gene mutations associated with anaplastic transformation of human thyroid carcinomas." Jpn J Cancer Res. 83(12):1293-8.
Nakamura et al., 2001, "Activation of calcineurin and stress activated protein kinase/p38-mitogen activated protein kinase in hearts of utrophin-dystrophin knockout mice." Neuromuscul Disord. 11(3):251-259.
Nakamura et al., 2001, "Stretch-activated cation channels in skeletal muscle myotubes from sarcoglycan-deficient hamsters." Am J Physiol Cell Physiol. 281(2):C690-699.
Nichols et al., 1994, "Function of von Willebrand factor after crossed bone marrow transplantation between normal and von Willebrand disease pigs: effect on arterial thrombosis in chimeras." Proc Natl Acad Sci U S A. 92(7):2455-9.
Nichols et al., 1995, "von Willebrand disease in the RIIIS/J mouse is caused by a defect outside of the von Willebrand factor gene." Blood. 83(11):3225-31. (Erratum in: Blood. Sep. 15, 1995;86(6):2461).
Ninomiya et al., 1997, "p53 gene mutation analysis in porokeratosis and porokeratosis-associated squamous cell carcinoma." J Dermatol Sci. 14(3):173-8.
Nishida et al., 1981, "Complement-dependent cytotoxicity in rats bearing human adenovirus type 12-induced primary retinoblastoma-like tumor in the eye." Curr Eye Res. 1(1):53-5.
Norrdin et al., 1995, "Bone changes in mucopolysaccharidosis VI in cats and the effects of bone marrow transplantation: mechanical testing of long bones." Bone. 17(5):485-9.
Oh et al., 2000, "Identification of p53 gene mutations in breast cancers and their effects on transcriptional activation function" Mol Cells. 10(3):275-80.
Okada et al., 1995, "Experimental and clinical studies on calcium urolithiasis: (I) Animal model for calcium oxalate urolithiasis using ethylene glycol and 1-alpha (OH) D3." Hinyokika Kiyo. 31(4):565-77 (In Japanese with English Abstract).
Onda et al., 1999, "Tsc2(+/−) mice develop tumors in multiple sites that express gelsolin and are influenced by genetic background." J Clin Invest. 104(6):687-95.
Otterbach & Stoffel, 1995, "Acid sphingomyelinase-deficient mice mimic the neurovisceral form of human lysosomal storage disease (Niemann-Pick disease)." Cell. 81(7):1053-61.
Pillers et al., 1999, "Normal cochlear function in mdx and mdx(Cv3) Duchenne muscular dystrophy mouse models." Laryngoscope. 109(8):1310-1312.
Popp et al., 1985, "Hematology of a murine beta-thalassemia: a longitudinal study." Ann N Y Acad Sci. 445:432-44.
Radig et al., 1998, "p53 gene mutations in osteosarcomas of low-grade malignancy." Hum Pathol. 29(11):1310-6.
Raja et al., 1994, "Intestinal iron absorption studies in mouse models of iron-overload." Br J Haematol. 86(1):156-62.
Rall et al., 1996, "Ki-ras and p53 mutations in pancreatic ductal adenocarcinoma." Pancreas.12(1):10-7.
Reipert et al., 2000, "Characterization of antibodies induced by human factor VIII in a murine knockout model of hemophilia A." Thromb Haemost. 84(5):826-32.
Richardson et al., 1998, "Vasculopathy and insulin resistance in the JCR:LA-cp rat." Atherosclerosis. 138(1):135-46.
Sanders et al., 1988, "Thrombotic thrombocytopenia with von Willebrand factor deficiency induced by botrocetin." An animal model. Lab Invest. 59(4):443-52.
Sango et al., 2002, "Lysosomal storage results in impaired survival but normal neurite outgrowth in dorsal root ganglion neurones from a mouse model of Sandhoff disease." Neuropathol Appl Neurobiol. 28(1):23-34.
Scharnhorst et al., 1997, "Differential regulation of the Wilms' tumor gene, WT1, during differentiation of embryonal carcinoma and embryonic stem cells." Cell Growth Differ. 8(2):133-43.

(56) References Cited

OTHER PUBLICATIONS

Schlenker and Burbach, 1991, "The dystrophic hamster: an animal model of alveolar hypoventilation." J Appl Physiol (1985). 71(5):1655-1662.
Schuyer et al., 1998, "High prevalence of codon 213Arg—>Stop mutations of the TP53 gene in human ovarian cancer in the southwestern part of the Netherlands." Int J Cancer. 76(3):299-303.
Seifman et al., 2001, "Functional effects of unilateral laser papillectomy in the pig." Urology. 57(4):832-6.
Shalev et al., 2014, "When Proteins Start to Make Sense: Fine-tuning Aminoglycosides for PTC Suppression Therapy. Medchemcomm." Med. Chem. Commun., 5(8):1092-1105.
Skow et al., 1983, "A mouse model for beta-thalassemia." Cell. 4(3):1043-52.
Snyder et al., 1999, "Correction of hemophilia B in canine and murine models using recombinant adeno-associated viral vectors." Nat Med. 5(1):64-70.
Stotland et al., 2000, "Mouse models of chronic lung infection with Pseudomonas aeruginosa: models for the study of cystic fibrosis." Pediatr Pulmonol 30(5):413-424.
Sweeney et al., 1990, "The RIIIS/J inbred mouse strain as a model for von Willebrand disease." Blood. 76(11):2258-65.
Tanaka et al., 1995, "Regulation of apolipoprotein B secretion in hepatocytes from Watanabe heritable hyperlipidemic rabbit, an animal model for familial hypercholesterolemia." Atherosclerosis. 114(1):73-82.
Tsutsumi et al., 2000, "Effects of NO-1886, a lipoprotein lipase promoting agent, on homozygous and heterozygous Watanabe heritable hyperlipidaemic rabbits." Arzneimittelforschung. 50(2):118-21.
Vail and Macewen, 2000, "Spontaneously occurring tumors of companion animals as models for human cancer." Cancer Invest. 18(8):781-92.
Valentine et al., 1992, "Canine X-linked muscular dystrophy as an animal model of Duchenne muscular dystrophy: a review." Am J Med Genet. 42(3):352-356.
Vierling JM. 2001, "Animal models for primary sclerosing cholangitis." Best Pract Res Clin Gastroenterol. 15(4):591-610.
Vogler et al., 2001, "A novel model of murine mucopolysaccharidosis type VII due to an intracisternal a particle element transposition into the beta-glucuronidase gene: clinical and pathologic findings." Pediatr Res. 49(3):342-8.
Vogler et al., 2001, "Murine mucopolysaccharidosis VII: impact of therapies on the phenotype, clinical course, and pathology in a model of a lysosomal storage disease." Pediatr Dev Pathol. 4(5):421-33.
Vollrath et al., 2001, Correction of the retinal dystrophy phenotype of the RCS rat by viral gene transfer of Mertk. Proc Natl Acad Sci U S A. 98(22):12584-9.
Vydrin, et al., 2003, "Component Composition of Gentamicin Sulfate Preparations." Pharmaceutical Chemistry Journal (Translation of Khimiko-Farmatsevticheskii Zhurnal) 37(8):448-450.
Wang et al., 1997, A factor IX-deficient mouse model for hemophilia B gene therapy. Proc Natl Acad Sci U S A. 94(21):11563-6.
Wang et al., 2001, "A novel, clinically relevant animal model of metastatic pancreatic adenocarcinoma biology and therapy." Int J Pancreatol. 29(1):37-46.
Wang-Gohrke et al., 1998, "Genomic semi-automated cycle sequencing as a sensitive screening technique for p53 mutations in frozen tumor samples." Oncol Rep. 5(1):65-8.
Windle et al., 1990, Mellon PL. Retinoblastoma in transgenic mice. Nature. 343(6259):665-9.
Wolfe et al., 2000, "Gene transfer of low levels of beta-glucuronidase corrects hepatic lysosomal storage in a large animal model of mucopolysaccharidosis VII." Mol Ther. 2(6):552-61.
Yang et al., 1999, "p53 mutations and protein overexpression in primary colorectal cancer and its liver metastasis." Zhonghua Zhong Liu Za Zhi. 21(2):114-8 (Original publication in Chinese with English Abstract only).
Zhang and Roth, 1994, "Anti-oncogene and tumor suppressor gene therapy—examples from a lung cancer animal model." In Vivo. 8(5):755-69.
Burke, J.F. and Mogg, A.E., "Suppression of a nonsense mutation in mammalian cells in vivo by the aminoglycoside antibiotics G-418 and paromomycin", Nucleic Acids Research, vol. 13 No. 17 1985, 6265-6272, XP009088534.
Huang, Chuan et al., "Delineating the Biosynthesis of Gentamicin X2, the Common Precursor of the Gentamicin C Antibiotic Complex", Chemistry & Biology 22, 251-261, Feb. 19, 2015, XP-002786176.
Karki, Suman et al., "Gene Inactivation Study on gntK, a Putative C-methyltransferase Gene in Gentamicin Biosynthesis from Micromonospora echinospora", J Korean Soc Appl Biol Chem (2012) 55, 439-442.

* cited by examiner

USE OF AN AMINOGLYCOSIDE FOR NONSENSE MUTATION SUPPRESSION AND THE TREATMENT OF DISEASE

This application is a U.S. national stage application of International Patent Application No. PCT/US2016/035709, filed Jun. 3, 2016, which claims the benefit of priority to U.S. Provisional Application Ser. No. 62/171,838, filed Jun. 5, 2015, which is incorporated herein by reference in its entirety and for all purposes.

1. FIELD OF INVENTION

Provided herein are methods for treating or preventing nonsense mutation mediated diseases associated with a germline or somatic nonsense mutation in DNA that result in a premature termination codon in mRNA by administering an aminoglycoside or a composition thereof.

2. BACKGROUND PROVIDED HEREIN

Gene expression in cells depends upon the sequential processes of transcription and translation. Together, these processes produce a protein from the nucleotide sequence of its corresponding gene.

Transcription involves the synthesis of mRNA from DNA by RNA polymerase. Transcription begins at a promoter region of the gene and continues until termination is induced, such as by the formation of a stem-loop structure in the nascent RNA or the binding of the rho gene product.

Protein is then produced from mRNA by the process of translation, occurring on the ribosome with the aid of tRNA, tRNA synthetases and various other protein and RNA species. Translation comprises three phases: initiation, elongation and termination. Translation is initiated by the formation of an initiation complex consisting of protein factors, mRNA, tRNA, cofactors and the ribosomal subunits that recognize signals on the mRNA that direct the translation machinery to begin translation on the mRNA.

Once the initiation complex is formed, growth of the polypeptide chain occurs by the repetitive addition of amino acids by the peptidyl transferase activity of the ribosome as well as tRNA and tRNA synthetases. The presence of one of the three termination codons (UAA, UAG, UGA) in the A site of the ribosome signals the polypeptide chain release factors (RFs) to bind and recognize the termination signal. Subsequently, the ester bond between the 3' nucleotide of the tRNA located in the ribosome's P site and the nascent polypeptide chain is hydrolyzed. The completed polypeptide chain is released, and the ribosome subunits are recycled for another round of translation.

Mutations of the DNA sequence in which the number of bases is altered are categorized as insertion or deletion mutations (frameshift mutations) and can result in major disruptions of the genome. Mutations of the DNA that change one base into another are labeled missense mutations and are subdivided into the classes of transitions (one purine to another purine, or one pyrimidine to another pyrimidine) and transversions (a purine to a pyrimidine, or a pyrimidine to a purine).

Insertions, deletions, transition and transversion mutations can all result in a nonsense mutation, or chain termination mutation, in which the base mutation or frameshift mutation changes an amino acid codon into one of the three stop codons. The resulting premature stop codon can produce an aberrant, partially functional or non-functional protein in cells as a result of premature translation termination. A nonsense mutation in an essential gene can be lethal and can also result in a number of nonsense mutation mediated diseases.

In bacterial and eukaryotic organisms with nonsense mutations, a nonsense mutation can arise as a result of a germline or somatic mutation in DNA that results in the production of a premature termination codon. Readthrough of the premature termination codon allows insertion of a near-cognate tRNA at the ribosomal A-site, leading to synthesis of a full-length protein from an otherwise defective mRNA. Small molecules that affect cellular processes involved in protein synthesis and/or the mRNA quality control process (among other quality control processes) can promote readthrough at premature termination codons. Readthrough at a premature termination codon results when an amino acid is incorporated into the growing polypeptide chain at the site of the premature termination codon. The inserted amino acid may not necessarily be identical to the original amino acid of the wild-type protein; however, many amino acid substitutions are well tolerated and do not have a deleterious effect on protein structure or function. Thus, a protein produced by the suppression of the premature termination codon would be likely to possess activity close to that of the wild-type protein. Such a result provides an opportunity to treat diseases associated with nonsense mutations by avoiding premature translation termination through suppression of the premature termination codon.

Aminoglycosides have been suggested as possible candidates for premature termination codon suppression therapy. See Shalev and Baasov, Medchemcomm., 2014 August 1; 5(8): 1092-1105. However, to date, no structures of the human A-site are known to complex with any of the available aminoglycosides that induce readthrough. Moreover, elucidation of the readthrough mechanism of the aminoglycoside complex known as gentamicin in eukaryotic systems remains to be determined. Id. Since aminoglycoside activity in eukaryotes is not fully understood, the rational design of new and improved derivatives remains complex. Id. Therefore, there remains a need for further elucidation of the biological activity of aminoglycosides and the identification of new derivatives that avoid known toxicities while conferring the benefits of readthrough protein production.

3. SUMMARY

Provided herein is Compound 1, pharmaceutical compositions thereof and methods of treatment therewith. Compound 1, pharmaceutical compositions thereof, and methods of treatment therewith are, in part, based upon the modulation of premature translation termination which plays a role in a variety of nonsense mutation mediated diseases. Without being limited by theory, such diseases can occur due to the decreased amount of active protein produced as a result of premature termination of translation. Compound 1 is believed to allow the translation of mRNA to continue past a nonsense mutation or a premature stop codon resulting to enable the production of full-length protein. Thus, provided herein is Compound 1, compositions thereof, and methods for their use for treating and preventing a variety of diseases, in particular nonsense mutation mediated diseases associated with premature translation termination.

Provided herein is Compound 1:

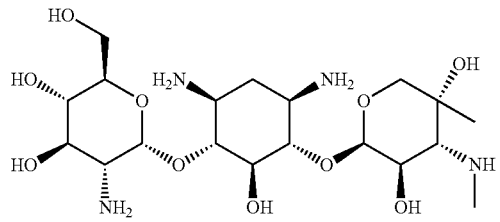

having the name (2R,3S,4R,5R,6S)-5-amino-6-(((1R,2S,3S, 4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-2-(hydroxymethyl)tetrahydro-2H-pyran-3,4-diol, and pharmaceutically acceptable polymorphs, prodrugs, salts, solvates, hydrates, and clathrates thereof (collectively referred to herein as "Compound 1"). The compound chemically named (2R,3S,4R,5R,6S)-5-amino-6-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-2-(hydroxymethyl)tetrahydro-2H-pyran-3,4-diol is disclosed and chromatographically separated as Gentamicin X in U.S. Pat. No. 3,915,955, granted on Oct. 28, 1975, the entirety of which is incorporated by reference herein.

In one embodiment, Compound 1 is a pharmaceutically acceptable salt, hydrate, clathrate, prodrug, polymorph, biohydrolyzable ester or purified stereoisomer including, but not limited to, an optically pure enantiomer or diastereomer.

Provided herein are methods of treating or preventing a nonsense mutation mediated disease by modulation of premature translation termination, a nonsense mutation or a premature stop codon, comprising administering to a patient in need thereof a therapeutically or prophylactically effective amount of Compound 1 or a pharmaceutical composition thereof. In one embodiment, the disease is a germline or somatic nonsense mutation mediated disease selected from the group consisting of a nonsense mutation mediated cancer, an inborn error of metabolism, autoimmune disease, a blood disease, a collagen disease, diabetes, a neurodegenerative disease, a proliferative disease, a cardiovascular disease, a pulmonary disease, an ocular disease, a ciliopathy disease, an inflammatory disease, a central nervous system (CNS) disease, a liver disease, a kidney disease, a muscular dystrophy and a lysosomal storage disease.

In another embodiment, the germline or somatic nonsense mutation mediated cancer is lung cancer, breast cancer, colon cancer, pancreatic cancer, non-Hodgkin's lymphoma, esophageal cancer, colorectal carcinoma, neurofibromatosis, retinoblastoma or Wilm's tumor. In another embodiment, the autoimmune disease is an immunodeficiency, rheumatoid arthritis or graft versus host disease. In another embodiment, the germline or somatic nonsense mutation mediated blood disease is a hemophilia, von Willebrand disease or b-thalassemia. In another embodiment, the diabetes is Type I diabetes or Type II diabetes. In other embodiments, the germline or somatic nonsense mutation mediated neurodegenerative disease is ataxia-telangiectasia. In other embodiments, the germline or somatic nonsense mutation mediated proliferative disease is tuberous sclerosis. In other embodiments, the germline or somatic nonsense mutation mediated cardiovascular disease is familial hypercholesterolemia. In another embodiment, the germline or somatic nonsense mutation mediated pulmonary disease is cystic fibrosis.

In another embodiment, the germline or somatic nonsense mutation mediated ocular disease is aniridia, choroideremia, renal-coloboma syndrome, Lebers congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy, corneal degeneration, optic nerve hypoplasia, retinal detachment, secondary strabismus or tunica vasculosa lentis. In another specific embodiment, the ocular disease is Usher syndrome type 2A. In certain specific embodiments, aniridia is familial aniridia or sporadic aniridia. In another specific embodiment, the aniridia is a symptom associated with WAGR (Wilms tumor-aniridia-genital anomalies-retardation) syndrome or Gillespie syndrome. In some embodiments, the gene is selected from the PAX6 gene, REP1 gene, CHD7 gene, PAX2 gene, or BBS2 gene.

In another embodiment, the germline or somatic nonsense mutation mediated liver disease is cirrhosis, In another embodiment, the germline or somatic nonsense mutation mediated ciliopathy disease is early embryonic death (some cases), hydrocephalus (some cases), polycystic liver disease or retinal degeneration (some forms). In another embodiment, the germline or somatic nonsense mutation mediated kidney disease is polycystic kidney disease or kidney stones. In another embodiment, the germline or somatic nonsense mutation mediated muscular dystrophy is Becker or Duchenne muscular dystrophy.

In another embodiment, the germline or somatic nonsense mutation mediated lysosomal storage disease is a germline or somatic nonsense mutation mediated mucopolysaccharidosis, Sandhoff disease or Niemann-Pick Disease Type C.

In other embodiments, the germline or somatic nonsense mutation mediated mucopolysaccharidosis is Hurler Syndrome (MPS IH), Hurler-Scheie Syndrome (MPS IH/S), Scheie Syndrome (MPS IS), Hunter Syndrome (MPS II), Sanfilippo Syndrome A (MPS IIIA), Sanfilippo Syndrome B (MPS IIIB), Sanfilippo Syndrome C (MPS IIIC), Sanfilippo Syndrome D (MPS IIID), Morquio syndrome A (MPS IVA), Morquio Syndrome B (MPS IVB), Maroteaux-Lamy Syndrome A (MPS VI), Sly Syndrome (MPS VII) or Natowicz Syndrome (MPS IX).

In some embodiments, provided herein are methods for modulating premature translation termination comprising administering Compound 1 or a pharmaceutical composition thereof to a patient in need thereof or contacting cell exhibiting premature translation termination with an effective amount of Compound 1 or a pharmaceutical composition thereof. In one embodiment, provided herein is a method for suppressing premature translation termination in a cell comprising administering Compound 1 or a pharmaceutical composition thereof to a patient in need thereof or contacting a cell exhibiting premature translation termination with an effective amount of Compound 1 or a pharmaceutical composition thereof. In one embodiment, provided herein is a method for inducing nonsense mutation suppression in a cell comprising administering Compound 1 or a pharmaceutical composition thereof to a patient in need thereof or contacting a cell exhibiting a nonsense mutation with an effective amount of Compound 1 or a pharmaceutical composition thereof. In some embodiments, provided herein are methods for inducing readthrough of a premature stop codon comprising administering Compound 1 or a pharmaceutical composition thereof to a patient in need thereof or contacting cell exhibiting premature translation termination with an effective amount of Compound 1 or a pharmaceutical composition thereof. A nonsense codon can be present in the DNA of any type of cell and can arise naturally or result from germline or somatic mutagenesis. Accordingly, cells encompassed by the present methods include animal cells, mammalian cells, bacterial cells, plant cells and virally infected cells. In one embodiment, the nonsense codon is present in the progenitor DNA. In another embodiment, the nonsense codon results from a germline mutation. In another embodiment, the nonsense codon results from somatic mutation.

Without being limited to any particular theory, the ability of Compound 1 to promote readthrough of a nonsense mutation or a premature stop codon makes it useful in the treatment or prevention of any disease which is caused in whole or in part by a nonsense mutation in DNA or a premature stop codon in mRNA. Such diseases can occur due to the decreased amount of active, functional protein produced as a result of premature termination of translation. Without being limited to any particular theory, Compound 1 is believed to allow the translation of mRNA to continue past the premature stop codon resulting in the production of full length protein.

3.1 Definitions

As used herein, the term "premature translation termination" refers to the result of a germline or somatic mutation that results in the change of a codon corresponding to an amino acid to a stop codon (UAG, UGA, UAA).

As used herein, the term "premature termination codon" or "premature stop codon" refers to the occurrence of a stop codon in mRNA where a codon corresponding to an amino acid should be.

As used herein, the term "nonsense mutation" refers to a germline or somatic mutation in DNA changing a codon corresponding to an amino acid in mRNA to a stop codon. In one embodiment, the nonsense mutation is a mutation that occurs in DNA and is then transcribed into mRNA.

As used herein, the term "nonsense suppression" refers to the inhibition or suppression of premature translation termination.

As used herein, the term "modulation of premature translation termination" refers to the upregulation of gene expression in the presence of a nonsense suppression agent. For example, if it is desirable to increase production of a functional active protein compared to avoiding the production of a defective protein encoded by a gene with a premature stop codon, i.e., to permit readthrough of the premature stop codon in the gene so translation of the mRNA can occur, such modulation of premature translation termination requires the use of a nonsense suppression agent.

As used herein, the term "dose(s)" means a quantity of active agent to be administered.

As used herein, the term "unit dosage form(s)" includes liquid dosage forms such as solutions suitable for parenteral administration to a patient.

As used herein, the terms "dosing regimen" and "dosage(s)" refer to the amount of an active agent given per unit and the duration of administration during a given time period to achieve a certain plasma concentration or functional therapeutic benefit.

As used herein, the terms "subject" and "patient" are used interchangeably to refer to an animal or any living organism having sensation and the power of voluntary movement, and which requires for its existence oxygen and organic food. Non-limiting examples include members of the human, primate, equine, porcine, bovine, leporine, *rattus*, murine, canine and feline species. In some embodiments, the subject is a mammal or a warm-blooded vertebrate animal. In certain embodiments, the subject is a non-human animal. In specific embodiments, the subject is a human. In certain embodiments, the subject is a fetus, embryo, infant, child, adolescent or adult. In one embodiment, it has been determined through pre-screening that the subject possesses a nonsense mutation. In another embodiment, it has been determined through genetic pre-screening which premature stop codon the patient has (i.e., UAA, UGA, or UAG) and the associated context (i.e., UAAG, UAAA, UAAC, UAAU, UGAG, UGAA, UGAC, UGAU, UAGG, UAGA, UAGC or UAGU).

As used herein, a "therapeutically effective amount" refers to that amount of Compound 1 sufficient to provide a functional therapeutic benefit in the treatment or management of the disease or to delay or minimize symptoms associated with the disease. Further, a therapeutically effective amount with respect to Compound 1 includes that amount alone, or in combination with other therapies, that provides a functional therapeutic benefit in the treatment or management of the disease. Used in connection with an amount of Compound 1, the term can encompass an amount that improves overall therapy, reduces or avoids symptoms or causes of disease, or enhances the therapeutic efficacy of or synergy with one or more therapeutic agents.

As used herein, a "prophylactically effective amount" refers to that amount of Compound 1 sufficient to result in the prevention, recurrence or spread of the disease. A prophylactically effective amount may refer to the amount of Compound 1 sufficient to prevent initial disease or the recurrence or spread of the disease in a patient, including but not limited to those patients predisposed to the disease (i.e., known to possess a gene(s) having one or more nonsense mutations). A prophylactically effective amount of Compound 1 may also refer to the amount that prevents the disease. Used in connection with an amount of Compound 1, the term can encompass an amount that improves overall prophylaxis or enhances the prophylactic efficacy of or synergy with another prophylactic agent.

As used herein, "in combination" refers to the use of more than one prophylactic and/or therapeutic agents coadministered with Compound 1.

As used herein, the terms "manage", "managing" and "management" refer to the beneficial effects that a subject having a nonsense mutation mediated disease derives from the administration of Compound 1, which administration may not result in the treatment or prevention of the nonsense mutation mediated disease. In certain embodiments, a subject is administered Compound 1 to "manage" a nonsense mutation mediated disease and prevent the progression or worsening of the disease.

As used herein, the terms "prevent", "preventing" and "prevention" refer to the administration of Compound 1 for the purpose of causing the onset, recurrence or spread of the nonsense mutation mediated disease to cease in a subject having such a disease.

As used herein, the terms "treat", "treating" and "treatment" refer to the administration of Compound 1 for the purpose of causing the eradication or amelioration of the nonsense mutation mediated disease or symptoms associated with the disease to cease in a subject. In certain embodiments, such terms refer to the administration of Compound 1 for the purpose of minimizing the spread or worsening of the nonsense mutation mediated disease in a subject having such a disease.

As used herein, the term "pharmaceutically acceptable salts" refer to salts prepared from pharmaceutically acceptable non-toxic acids including inorganic acids and organic acids. Suitable pharmaceutically acceptable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, phosphonic, propionic, salicylic, stearic, succinic, sulfanilic, sulfate, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. In one embodiment, Compound 1 is provided as the sulfate salt. Other examples of salts are well known in the art, see, e.g., *Remington's Pharmaceutical Sciences,* 18th ed., Mack Publishing, Easton Pa. (1990).

As used herein and unless otherwise indicated, the term "prodrug" means a derivative of a compound that can hydrolyze, oxidize, or otherwise react under biological conditions (in vitro or in vivo) to provide an active compound, particularly Compound 1. Examples of prodrugs include, but are not limited to, derivatives and metabolites of Compound 1 that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the terms "optically pure" or "stereomerically pure" mean that the stereoisomer of a compound is substantially free of the other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, "in combination" in the context of the administration of therapies refers to the use of more than one therapy. The use of the term "in combination" does not restrict the order in which therapies are administered to a subject with a nonsense mutation mediated disease. In certain embodiments, administration of one or more therapies to a subject with such a disease includes, without limitation, a first therapy that can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which has been identified as having such a disease. The therapies are administered to a subject in a sequence and within a time interval such that a unit dosage form(s) described herein can act together with another therapy to provide an increased benefit than if the therapies were administered alone.

As used herein, the terms "about" or "approximately" mean an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocycle and heteroaromatic amines, and polyether amines.

In one embodiment, Compound 1 is a member of a "gentamicin complex."

In another embodiment, Compound 1 is administered independently of the "gentamicin complex." In another embodiment, Gentamicin C2 is administered independently of the "gentamicin complex." In another embodiment, Compound 1 is administered in combination with Gentamicin C2.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers thereof.

4. DETAILED DESCRIPTION

4.1 Compound 1

Provided herein is Compound 1:

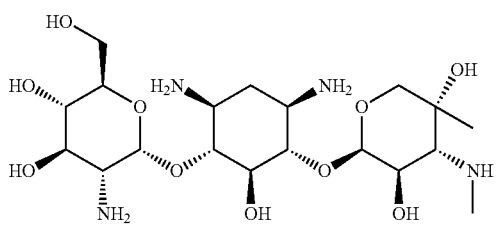

having the name (2R,3S,4R,5R,6S)-5-amino-6-((((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-2-(hydroxymethyl)tetrahydro-2H-pyran-3,4-diol, including pharmaceutically acceptable polymorphs, prodrugs, salts, solvates, hydrates, and clathrates thereof.

In one embodiment, Compound 1 is substantially free of other stereoisomers of Compound 1. In another embodiment, Compound 1 is substantially free of other diastereomers of Compound 1. In even another embodiment, Compound 1 is substantially free of other enantiomers of Compound 1. In another embodiment, Compound 1 is substantially free of other compounds of the gentamicin complex. In certain embodiments, Compound 1 that is substantially pure contains less than about 10%, 9%, 8%, 7%, 6%, 5%, 4%, 3%, 2%, 1%, 0.5%, 0.4%, 0.3%, 0.2%, 0.1%, 0.05%, or 0.01% of one or more members of the gentamicin complex on a weight basis.

Compound 1 can be prepared and isolated according to the methods described in U.S. Pat. No. 3,915,955, the disclosure of which is incorporated by reference herein in its entirety.

4.2 Biological Assays and Animal Studies

Compounds that modulate premature translation termination can be identified by a number of techniques. For example, methods for screening compounds that modulate the post-transcriptional expression of any gene with a premature translation stop codon are described in International Patent Publication No. WO 01/44516 A2, incorporated herein in its entirety by reference. In one embodiment, an mRNA transcript encoded with a premature termination codon is translated in vitro and is used to screen a library of test compounds. In one embodiment, the mRNA transcript encoded with a premature termination codon is a reporter gene mRNA transcript encoded with a premature termination codon.

Two assays are developed for use in high throughput screens to identify small molecules that promote nonsense suppression. Each assay uses luciferase because luciferase is a functional reporter gene (light is only produced if the protein is functional), providing an extremely sensitive readout (light intensity is proportional to luciferase concentration in the nM range). The first assay is an in-vivo cell-based luciferase reporter assay and the second is a biochemical in-vitro cell-free assay consisting of rabbit reticulocyte lysate and a nonsense-containing luciferase reporter mRNA transcript. In the cell-based assay, a luciferase reporter construct containing a UGA, UAA or UAG premature termination codon is stably transfected in 293T Human Embryonic Kidney cells. In the biochemical assay, mRNA containing a UGA, UAA or UAG premature termination codon is used as a reporter in an in vitro translation reaction using rabbit reticulocyte lysate supplemented with tRNA, hemin, creatine kinase, amino acids, KOAc, Mg(OAc)2, and creatine phosphate. Translation of the mRNA is initiated within a virus derived leader sequence, which significantly reduces the cost of the assay because capped RNA is not required. Synthetic mRNA is prepared in vitro using the T7 promoter and the MegaScript in vitro transcription kit (Ambion).

Animal model systems can also be used to demonstrate the safety and efficacy of Compound 1. Compound 1 can be tested for biological activity using animal models for a disease, condition, or syndrome of interest. These include animals engineered to contain the target RNA element coupled to a functional readout system, such as a transgenic mouse.

Examples of animal models engineered to have one or more premature stop codons in the CFTR gene resulting in cystic fibrosis include, but are not limited to, cftr(−/−) mice (see, e.g., Freedman et al., 2001, Gastroenterology 121(4): 950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr(m1UNC)/Cftr(m1UNC) knockout mice (see, e.g., Stotland et al., 2000, Pediatr Pulmonol 30(5):413-24).

Examples of animal models engineered to have one or more premature stop codons in the dystrophin gene resulting in a muscular dystrophy include, but are not limited to, mouse, hamster, cat, dog, and C. elegans. Examples of mouse models include, but are not limited to, the dy−/− mouse (see, e.g., Connolly et al., 2002, J Neuroimmunol 127(1-2):80-7), with myositis (mdm) mouse mutation (see, e.g., Garvey et al., 2002, Genomics 79(2):146-9), the mdx mouse (see, e.g., Nakamura et al., 2001, Neuromuscul Disord 11(3):251-9), the utrophin-dystrophin knockout (dko) mouse (see, e.g., Nakamura et al., 2001, Neuromuscul Disord 11(3):251-9), the dy/dy mouse (see, e.g., Dubowitz et al., 2000, Neuromuscul Disord 10(4-5):292-8), the mdx (Cv3) mouse model (see, e.g., Pillers et al., 1999, Laryngoscope 109(8):1310-2), and the myotonic ADR-MDX mutant mice (see, e.g., Kramer et al., 1998, Neuromuscul Disord 8(8):542-50) and the like known to those skilled in the art. Examples of hamster models for muscular dystrophy include, but are not limited to, sarcoglycan-deficient hamsters (see, e.g., Nakamura et al., 2001, Am J Physiol Cell Physiol 281(2):C690-9) and the BIO 14.6 dystrophic hamster (see, e.g., Schlenker & Burbach, 1991, J Appl Physiol 71(5):1655-62). An example of a feline model for muscular dystrophy includes, but is not limited to, the hypertrophic feline muscular dystrophy model (see, e.g., Gaschen & Burgunder, 2001, Acta Neuropathol (Berl) 101(6):591-600). Canine models for muscular dystrophy include, but are not limited to, golden retriever muscular dystrophy (see, e.g., Fletcher et al., 2001, Neuromuscul Disord 11(3):239-43) and canine X-linked muscular dystrophy (see, e.g., Valentine et al., 1992, Am J Med Genet 42(3):352-6). Examples of C. elegans models for muscular dystrophy are described in Chamberlain & Benian, 2000, Curr Biol 10(21):R795-7 and Culetto & Sattelle, 2000, Hum Mol Genet 9(6):869-77.

Examples of animal models engineered to have one or more premature stop codons in a gene resulting in familial hypercholesterolemia include, but are not limited to, mice lacking functional LDL receptor genes (see, e.g., Aji et al., 1997, Circulation 95(2):430-7), Yoshida rats (see, e.g., Fantappiè et al., 1992, Life Sci 50(24):1913-24), the JCR:LA-cp rat (see, e.g., Richardson et al., 1998, Atherosclerosis 138 (1):135-46), swine (see, e.g., Hasler-Rapacz et al., 1998, Am J Med Genet 76(5):379-86), and the Watanabe heritable hyperlipidaemic rabbit (see, e.g., Tsutsumi et al., 2000, Arzneim.-Forsch./Drug Res. 50(I), 118-21; Harsch et al., 1998, Br J Pharmacol 124(2):277-82; and Tanaka et al., 1995, Atherosclerosis 114(1):73-82).

An example of an animal model engineered to have one or more premature stop codons in a tumor suppressor gene resulting in human cancer in general includes, but is not limited to, spontaneously occurring tumors of companion animals (see, e.g., Vail & MacEwen, 2000, Cancer Invest 18(8):781-92). Examples of animal models engineered to have one or more premature stop codons in a tumor suppressor gene resulting in lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model engineered to have one or more premature stop codons in a tumor suppressor gene resulting in breast cancer includes, but is not limited to, a transgenic mouse that overexpresses cyclin D1 (see, e.g., Hosokawa et al., 2001, Transgenic Res 10(5):471-8). An example of an animal model engineered to have one or more premature stop codons in a tumor suppressor gene resulting in colon cancer includes, but is not limited to, a TCRbeta and p53 double knockout mouse (see, e.g., Kado et al., 2001, Cancer Res 61(6):2395-8). Examples of animal models engineered to have one or more premature stop codons in a tumor suppressor gene resulting in pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models engineered to have one or more premature stop codons in a tumor suppressor gene resulting in non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model engineered to have one or more premature stop codons in a tumor suppressor gene resulting in esophageal cancer includes, but is not limited to, a mouse transgenic for the human papillomavirus type 16 E7 oncogene (see, e.g., Herber et al., 1996, J Virol 70(3):1873-81). Examples of animal models engineered to have one or more premature stop codons in a tumor suppressor gene resulting in colorectal carcinomas include, but are not limited to, Apc mouse models (see, e.g., Fodde & Smits, 2001, Trends Mol Med 7(8):369-73 and Kuraguchi et al., 2000, Oncogene 19(50): 5755-63). An example of an animal model engineered to have one or more premature stop codons in a tumor suppressor gene resulting in neurofibromatosis includes, but is not limited to, mutant NF1 mice (see, e.g., Cichowski et al., 1996, Semin Cancer Biol 7(5):291-8). Examples of animal models engineered to have one or more premature stop codons in a tumor suppressor gene resulting in retinoblastoma include, but are not limited to, transgenic mice that expression the simian virus 40 T antigen in the retina (see, e.g., Howes et al., 1994, Invest. Ophthalmol. Vis. Sci., 35(2):342-51 and Windle et al, 1990, Nature 343(6259):665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models engineered to have one or more premature stop codons in a tumor suppressor gene resulting in Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

In a specific embodiment, the gene is associated with a nonsense mutation mediated ocular disease. In certain embodiments, the ocular disease is aniridia, choroideremia, renal-coloboma syndrome, Lebers congenital amaurosis, retinitis pigmentosa, Bardet-Biedl syndrome, glaucoma, foveal hypoplasia, cataracts, Usher syndrome, central auditory processing difficulties, chorioretinal degeneration, congenital lens opacities, elevated intraocular pressure, exudative vascular retinopathy, glaucoma, iris hypoplasia, keratopathy (corneal degeneration), optic nerve hypoplasia, retinal detachment, secondary strabismus or tunica vasculosa lentis. In another specific embodiment, the ocular disease is Usher syndrome type 2A. In certain specific embodiments, aniridia is familial aniridia or sporadic aniridia. In another specific embodiment, the aniridia is a symptom associated with WAGR (Wilms tumor-aniridia-genital anomalies-retardation) syndrome or Gillespie syndrome. In some embodiments, the gene is selected from the PAX6 gene, REP1 gene, CHD7 gene, PAX2 gene, or BBS2 gene.

Examples of animal models engineered to have one or more premature stop codons in a gene resulting in retinitis pigmentosa include, but are not limited to, the Royal College of Surgeons ("RCS") rat (see, e.g., Vollrath et al., 2001, Proc Natl Acad Sci USA 98(22); 12584-9 and Hanitzsch et al., 1998, Acta Anat (Basel) 162(2-3):119-26), a rhodopsin knockout mouse (see, e.g., Jaissle et al., 2001, Invest. Ophthalmol. Vis. Sci., 42(2):506-13), and Wag/Rij rats (see, e.g., Lai et al., 1980, Am J Pathol 98(1):281-4).

Examples of animal models engineered to have one or more premature stop codons in a gene resulting in aniridia include, but are not limited to, Hill, R., et al., 1991, "Mouse Small eye results from mutations in a paired-like homeobox-containing gene," *Nature* 354(6354):522-525 and Gregory-Evans, C., et al., "Postnatal manipulation of Pax6 dosage reverses congenital tissue malformation defects," *J. Clin. Invest.* 2014; 124(1): 111-116. doi: 10.1172/JCI70462, both of which are incorporated by reference herein in their entirety.

Examples of animal models engineered to have one or more premature stop codons in a gene resulting in cirrhosis include, but are not limited to, $CCl_4$-exposed rats (see, e.g., Kloehn et al., 2001, Horm Metab Res 33(7):394-401) and rodent models instigated by bacterial cell components or colitis (see, e.g., Vierling, 2001, Best Pract Res Clin Gastroenterol 15(4):591-610).

Examples of animal models engineered to have one or more premature stop codons in a gene resulting in hemophilia include, but are not limited to, rodent models for hemophilia A (see, e.g., Reipert et al., 2000, Thromb Haemost 84(5):826-32; Jarvis et al., 1996, Thromb Haemost 75(2):318-25; and Bi et al., 1995, Nat Genet 10(1):119-21), canine models for hemophilia A (see, e.g., Gallo-Penn et al., 1999, Hum Gene Ther 10(11):1791-802 and Connelly et al, 1998, Blood 91(9); 3273-81), murine models for hemophilia B (see, e.g., Snyder et al., 1999, Nat Med 5(1):64-70; Wang et al., 1997, Proc Natl Acad Sci USA 94(21):11563-6; and Fang et al., 1996, Gene Ther 3(3):217-22), canine models for hemophilia B (see, e.g., Mount et al., 2002, Blood 99(8): 2670-6; Snyder et al., 1999, Nat Med 5(1):64-70; Fang et al., 1996, Gene Ther 3(3):217-22); and Kay et al., 1994, Proc Natl Acad Sci USA 91(6):2353-7), and a rhesus macaque model for hemophilia B (see, e.g., Lozier et al., 1999, Blood 93(6):1875-81).

Examples of animal models engineered to have one or more premature stop codons in a gene resulting in von Willebrand disease include, but are not limited to, an inbred mouse strain RIIIS/J (see, e.g., Nichols et al., 1994, 83(11): 3225-31 and Sweeney et al., 1990, 76(11):2258-65), rats injected with botrocetin (see, e.g., Sanders et al., 1988, Lab Invest 59(4):443-52), and porcine models for von Willebrand disease (see, e.g., Nichols et al., 1995, Proc Natl Acad Sci USA 92(7):2455-9; Johnson & Bowie, 1992, J Lab Clin Med 120(4):553-8); and Brinkhous et al., 1991, Mayo Clin Proc 66(7):733-42).

Examples of animal models engineered to have one or more premature stop codons in a gene resulting in b-thalassemia include, but are not limited to, murine models with mutations in globin genes (see, e.g., Lewis et al., 1998, Blood 91(6):2152-6; Raja et al., 1994, Br J Haematol 86(1):156-62; Popp et al., 1985, 445:432-44; and Skow et al., 1983, Cell 34(3):1043-52).

Examples of animal models engineered to have one or more premature stop codons in a gene resulting in kidney stones include, but are not limited to, genetic hypercalciuric rats (see, e.g., Bushinsky et al., 1999, Kidney Int 55(1):234-43 and Bushinsky et al., 1995, Kidney Int 48(6):1705-13), chemically treated rats (see, e.g., Grases et al., 1998, Scand J Urol Nephrol 32(4):261-5; Burgess et al., 1995, Urol Res 23(4):239-42; Kumar et al., 1991, J Urol 146(5):1384-9; Okada et al., 1985, Hinyokika Kiyo 31(4):565-77; and Bluestone et al., 1975, Lab Invest 33(3):273-9), hyperoxaluric rats (see, e.g., Jones et al., 1991, J Urol 145(4):868-74), pigs with unilateral retrograde flexible nephroscopy (see, e.g., Seifman et al., 2001, UROLOGY 57(4):832-6), and rabbits with an obstructed upper urinary tract (see, e.g., Itatani et al., 1979, Invest Urol 17(3):234-40).

Examples of animal models engineered to have one or more premature stop codons in a gene resulting in ataxia-telangiectasia include, but are not limited to, murine models of ataxia-telangiectasia (see, e.g., Barlow et al., 1999, Proc Natl Acad Sci USA 96(17):9915-9 and Inoue et al., 1986, Cancer Res 46(8):3979-82).

Examples of animal models engineered to have one or more premature stop codons in a gene resulting in a nonsense mutation mediated lysosomal storage disease include, but are not limited to, mouse models for a nonsense mutation mediated mucopolysaccharidosis including those for a mucopolysaccharidosis (MPS) disease selected from Hurler Syndrome (MPS IH), Hurler-Scheie Syndrome (MPS IH/S), Scheie Syndrome (MPS IS, formerly MPS V), Hunter Syndrome (MPS II), mouse models for Sanfilippo Syndrome A (MPS IIIA, also referred to as Sulfamidase deficiency) (see, e.g., Bhattacharyya et al., 2001, Glycobiology 11(1):99-103 and Bhaumik et al., 1999, Glycobiology 9(12):1389-96), Sanfilippo Syndrome B (MPS IIIB, also referred to as NAGLU deficiency), Sanfilippo Syndrome C (MPS IIIC), Sanfilippo Syndrome D (MPS IIID), Morquio Syndrome A (MPS IVA), Morquio Syndrome B (MPS IVB), feline models of Maroteaux-Lamy Syndrome A (MPS VI, also referred to as Arylsulfatase B (ARSB) deficiency) (see, e.g., Crawley et al., 1998, J Clin Invest. 101(1):109-19 and Norrdin et al., 1995, Bone 17(5):485-9), Sly Syndrome (MPS VII, also referred to as GUSB Deficiency) (see, e.g., Brooks et al., 2002, Proc Natl Acad Sci USA. 99(9):6216-21; Monroy et al., 2002, Bone 30(2):352-9; Vogler et al., 2001, Pediatr Dev Pathol. 4(5):421-33; Vogler et al., 2001, Pediatr Res. 49(3): 342-8; and Wolfe et al., 2000, Mol Ther. 2(6):552-561) and Natowicz Syndrome (MPS IX, also referred to as Hyaluronidase Deficiency); a mouse model of Sandhoff disease (see, e.g., Sango et al., 2002, Neuropathol Appl Neurobiol. 28(1): 23-34), arylsulfatase A (ASA)-deficient mouse model for metachromatic leukodystrophy (see, e.g., D'Hooge et al., 1999, Brain Res. 847(2):352-6 and D'Hooge et al, 1999, Neurosci Lett. 273(2):93-6; Matzner et al., 2002, Gene Ther. 9(1):53-63); mice with an aspartylglucosaminuria mutation (see, e.g., Jalanko et al., 1998, Hum Mol Genet. 7(2):265-72); a feline model of Niemann-Pick disease type C (see, e.g., March et al., 1997, Acta Neuropathol (Berl). 94(2):164-72); acid sphingomyelinase-deficient mice (see, e.g., Otterbach & Stoffel, 1995, Cell 81(7):1053-6), and bovine mannosidosis (see, e.g., Jolly et al., 1975, Birth Defects Orig. Arctic. Ser. XI(6):273-8).

Examples of animal models engineered to have one or more premature stop codons in a gene resulting in tuberous sclerosis ("TSC") include, but are not limited to, a mouse model of TSC1 (see, e.g., Kwiatkowski et al., 2002, Hum Mol Genet. 11(5):525-34), a Tsc1 (TSC1 homologue) knockout mouse (see, e.g., Kobayashi et al., 2001, Proc Natl Acad Sci USA. 2001 Jul. 17; 98(15):8762-7), a TSC2 gene mutant(Eker) rat model (see, e.g., Hino 2000, Nippon Rinsho 58(6):1255-61; Mizuguchi et al., 2000, J Neuropathol Exp Neurol. 59(3):188-96; and Hino et al., 1999, Prog Exp Tumor Res. 35:95-108); and Tsc2(+/−) mice (see, e.g., Onda et al., 1999, J Clin Invest. 104(6):687-95).

4.3 Methods of Use

Provided herein are methods of treating or preventing nonsense mutation mediated diseases or disorders by the suppression of premature translation termination, or enabling readthrough of a premature stop codon in a patient, which comprise administering to a patient in need of such treatment or prevention a therapeutically effective amount of Compound 1 or a pharmaceutical composition thereof.

In one embodiment, provided herein is a method for treating or preventing a disease associated with premature translation termination, a nonsense mutation or a premature stop codon, comprising administering to a patient having said disease an effective amount of Compound 1 or a pharmaceutical composition thereof.

In one embodiment, provided herein are methods for the treatment or prevention of any disease that is associated with a gene resulting from premature translation termination. In one embodiment, the disease is due, in part, to the lack of expression of the gene resulting from a premature stop codon. Specific examples of genes which may exhibit premature translation termination and diseases associated with premature translation termination are found in U.S. Pat. No. 7,291,461, titled: Methods For Identifying Small Molecules That Modulate Premature Translation Termination And Nonsense Mediated mRNA Decay, which is incorporated herein by reference in its entirety.

In some embodiments, the patient is a mammal, more preferably a human susceptible to or at risk of acquiring a genetic disease. In an alternative embodiment, the patient has undergone a screening process to determine the presence of a nonsense mutation comprising the steps of screening a subject or cells extracted therefrom by an acceptable nonsense mutation screening assay. In a related embodiment, the therapy is personalized in that the patient is screened for a nonsense mutation screening assay and treated by the administration of Compound 1. In a further embodiment, the patient is an infant or child. In yet another embodiment, provided herein is the treatment of pregnant woman or the fetus directly.

In certain embodiments, the nonsense mutation mediated diseases associated with a gene exhibiting premature translation termination, a nonsense mutation or a premature stop codon include, but are not limited to: a germline or somatic nonsense mutation mediated disease, selected from the group consisting of a nonsense mutation mediated cancer, an inborn error of metabolism, an autoimmune disease, a blood disease, a collagen disease, diabetes, a neurodegenerative disease, a proliferative disease, a cardiovascular disease, a pulmonary disease, an ocular disease, a ciliopathy disease, an inflammatory disease, a central nervous system (CNS) disease, a liver disease, a kidney disease, a muscular dystrophy and a lysosomal storage disease.

In one embodiment, the autoimmune disease is an immunodeficiency, rheumatoid arthritis or graft versus host disease.

In one embodiment, the blood disease is hemophilia, Von Willebrand disease or b-thalassemia.

In another embodiment, the diabetes is Type I diabetes or Type II diabetes.

In one embodiment, the neurodegenerative disease is ataxia-telangiectasia.

In one embodiment, the proliferative disease is tuberous sclerosis.

In one embodiment, the cardiovascular disease is familial hypercholesterolemia.

In one embodiment, the inflammatory disease is arthritis.

In one embodiment, the CNS disease is multiple sclerosis, Alzheimer's disease, Tay Sachs disease, LINCL or Parkinson's disease.

In one embodiment, the lysosomal storage disease is tuberous sclerosis, a mucopolysaccharidosis (MPS) disease selected from Hurler syndrome (MPS IH), Hurler-Scheie syndrome (MPS IH/S), Scheie syndrome (MPS IS, formerly MPS V), Hunter syndrome (MPS II), Sanfilippo syndrome A (MPS IIIA, also referred to as Sulfamidase deficiency), Sanfilippo syndrome B (MPS IIIB, also referred to as NAGLU deficiency), Sanfilippo syndrome C (MPS IIIC), Sanfilippo syndrome D (MPS IIID), Morquio syndrome A (MPS IVA), Morquio syndrome B (MPS IVB), Maroteaux-Lamy syndrome A (MPS VI, also referred to as ARSB deficiency), Sly syndrome (MPS VII, also referred to as GUSB deficiency), Natowicz syndrome (MPS IX, also referred to as Hyaluronidase deficiency), metachromatic leukodystrophy, Niemann Pick's disease or Sandhoff disease.

In one embodiment, the kidney disease is polycystic kidney disease or kidney stones.

In one embodiment, the collagen disease is osteogenesis imperfecta, Marfan syndrome, or cirrhosis.

In one embodiment, the pulmonary disease is cystic fibrosis.

In one embodiment, the ocular disease is aniridia.

In one embodiment, the muscular dystrophy is Becker or Duchenne muscular dystrophy.

In one embodiment, the cardiovascular disease is familial hypercholesterolemia or atherosclerosis.

Specific nonsense mutation mediated diseases within the scope of the methods provided herein include, but are not limited to, amyloidosis, aniridia, arthritis, hemophilia, Alzheimer's disease, Tay Sachs disease, LINCL, atherosclerosis, giantism, dwarfism, hypothyroidism, hyperthyroidism, aging, obesity, Parkinson's disease, Niemann Pick's disease, cystic fibrosis, heart disease, kidney stones, ataxia-telangiectasia, familial hypercholesterolemia, retinitis pigmentosa, tuberous sclerosis, Duchenne muscular dystrophy, myotonic dystrophy, multiple sclerosis, Marfan syndrome, Von Willebrand disease, b-thalassemia, Type I or Type II diabetes, tuberous sclerosis, (MPS IH), Hurler-Scheie syndrome (MPS IH/S), Scheie syndrome (MPS IS, formerly MPS V), Hunter syndrome (MPS II), Sanfilippo syndrome A (MPS IIIA, also referred to as Sulfamidase deficiency), Sanfilippo syndrome B (MPS IIIB, also referred to as NAGLU deficiency), Sanfilippo syndrome C (MPS IIIC), Sanfilippo syndrome D (MPS IIID), Morquio syndrome A (MPS IVA), Morquio syndrome B (MPS IVB), Maroteaux-Lamy syndrome A (MPS VI, also referred to as ARSB deficiency), Sly syndrome (MPS VII, also referred to as GUSB deficiency), Natowicz syndrome (MPS IX), metachromatic leukodystrophy, Sandhoff disease and osteogenesis imperfecta.

In one embodiment, the nonsense mutation mediated cancer is of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals, or wherein the cancer is a solid tumor selected from sarcoma, carcinoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acute nonlymphocycytic leukemia, acute undifferentiated leukemia, chronic myelocytic leukemia, chronic lymphocytic leukemia, hairy cell leukemia or multiple myeloma. Both nonsense mutation mediated solid tumor and other cancers are included within the methods provided here.

In one embodiment, the cancer associated with a germline or somatic nonsense mutation in a tumor suppressor gene (see e.g. Garinis et al. 2002, Hum Genet 111:115-127; Wu et al., 1998, *Proc. Natl. Acad. Sci. USA,* 95: 15587-15591; Kung et al. 2000, Nature Medicine 6(12): 1335-1340) including, but not limited to, a gene selected from APC, ATM, BRAC1, BRAC2, MSH1, pTEN, Rb and p53. In particular embodiments, the mutation in a tumor suppressor gene results in expression of an mRNA transcript containing one or more premature stop codons.

In one embodiment, the tumor suppressor gene is the p53 gene. Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-42; Kajiyama et al., 1998, Dis Esophagus. 11(4): 279-83; Kawamura et al., 1999, Leuk Res. 23(2):115-26; Radig et al., 1998, Hum Pathol. 29(11):1310-6; Schuyer et al., 1998, Int J Cancer 76(3):299-303; Wang-Gohrke et al., 1998, Oncol Rep. 5(1):65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8): 1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any disease associated with a p53 gene encoding a premature translation codon including, but not limited to, the nonsense mutations described in the references cited above, can be treated or prevented by Compound 1.

In one embodiment, provided herein are methods of treating or preventing a disease by modulation of premature translation termination comprising contacting a cell with an effective amount of Compound 1 or a composition thereof. Cells encompassed by the present methods include animal cells, mammalian cells, bacterial cells, plant cells and virally infected cells. In one embodiment, the nonsense codon was present in the progenitor DNA. In another embodiment, the nonsense codon resulted from germline mutation. In another embodiment, the nonsense codon resulted from somatic mutation.

In certain embodiments, Compound 1 is administered to a patient, preferably a mammal, more preferably a human, as a preventative measure against a disease associated with premature translation termination, a nonsense mutation or a premature stop codon.

In one embodiment, it is first determined that the patient is suffering from a disease associated with premature translation termination, a nonsense mutation or a premature stop codon. In another embodiment, the patient has undergone a screening process to determine the presence of a nonsense mutation comprising the steps of screening a subject, or cells extracted therefrom, by an acceptable nonsense mutation screening assay. In one embodiment, the DNA of the patient can be sequenced or subject to Southern Blot, polymerase chain reaction (PCR), use of the Short Tandem Repeat (STR), or polymorphic length restriction fragments (RFLP) analysis to determine if a nonsense mutation is present in the DNA of the patient. Alternatively, it can be determined if altered levels of the protein or truncated protein resulting from a nonsense mutation are expressed in the patient by western blot or other immunoassays. In another embodiment, the patient is an unborn child who has undergone screening in utero for the presence of a nonsense mutation. Administration of Compound 1 can occur either before or after birth. In a related embodiment, the therapy is personalized in that the patient is screened for a nonsense mutation screening assay and treated by the administration of one or more compounds provided here; particularly, the patient may be treated with a compound particularly suited for the mutations in question; e.g., depending upon the disease type, cell type, and the gene in question. Such methods are well known to one of skill in the art.

In another embodiment, the cells (e.g., animal cells, mammalian cells, bacterial cells, plant cells and virally infected cells) are screened for premature translation termination, a nonsense mutation or a premature stop codon with a method such as that described above (i.e., the DNA of the cell can be sequenced or subjected to Southern Blot, polymerase chain reaction (PCR), use of the Short Tandem Repeat (STR), or polymorphic length restriction fragments (RFLP) analysis to determine if a nonsense mutation is present in the DNA of the cell).

In another embodiment, Compound 1 can be used in combination with an agent that inhibits the nonsense mediated mRNA decay pathway (NMDI-1, caffeine, and the like). In another embodiment, Compound 1 can be used in combination with an agent that suppresses premature termination codons (ataluren, other aminoglycosides, RTC13, RTC14 and the like) and allows readthrough.

In certain embodiments, Compound 1 can be administered in combination with an anticancer agent. Suitable anticancer agents include, but are not limited to, alkylating agents; nitrogen mustards; folate antagonists; purine antagonists; pyrimidine antagoinists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan and taxol.

The magnitude of a prophylactic or therapeutic dose of Compound 1 in the acute or chronic management of a disease or condition will vary, however, with the nature and severity of the disease or condition, and the route by which Compound 1 is administered. The dose, and perhaps the dose frequency, will also vary according to the age, body weight, and response of the individual patient. Suitable dosing regimens can be readily selected by those skilled in the art with due consideration of such factors.

4.4 Pharmaceutical Compositions

Provided herein are pharmaceutical compositions and single unit dosage forms comprising Compound 1. Individual dosage forms provided herein may be suitable for parenteral (including subcutaneous, intramuscular, bolus injection, intraarterial, or intravenous) administration.

Pharmaceutical compositions and dosage forms provided herein comprise Compound 1, or a pharmaceutically acceptable prodrug, polymorph, salt, solvate, hydrate, or clathrate thereof. Pharmaceutical compositions and dosage forms provided herein typically also comprise one or more pharmaceutically acceptable excipients.

Single unit dosage forms provided herein are suitable for parenteral (e.g., subcutaneous, intravenous, bolus injection, intramuscular, or intraarterial) administration to a patient. Examples of dosage forms include, but are not limited to: liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of inflammation or a related disease may contain a greater amount of Compound 1. A dosage form for acute treatment may contain more of an active ingredient than a dosage form used in the chronic treatment of the same disease. Similarly, a parenteral dosage form may contain a smaller amount of Compound 1 than an oral dosage form used to treat the same disease or disorder. These and other ways in which specific dosage forms are provided herein will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on Compound 1 in the dosage form.

4.4.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of Compound 1 disclosed herein can also be incorporated into the parenteral dosage forms provided herein.

4.4.2 Mucosal Dosage Forms

Mucosal dosage forms provided herein include, but are not limited to, ocular solutions, sprays and aerosols, or other forms known to one of skill in the art. See, e.g., *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985).

Suitable excipients (e.g., carriers and diluents) and other materials that can be used to provide mucosal dosage forms provided herein are well known to those skilled in the pharmaceutical arts, and depend on the particular site or method which a given pharmaceutical composition or dosage form will be administered. Examples of such additional ingredients are well known in the art. See, e.g., Remington's Pharmaceutical Sciences, 18th eds., Mack Publishing, Easton Pa. (1990).

5. EXAMPLES 5.1 Premature Stop Codon Readthrough

Table 1 shows the median concentration (aM) that doubles ($EC_{2x}$) the intensity of the nonsense suppression induced by Compound 1 alone as determined by enzyme-linked immunosorbent assay. Table 1 also provides the median maximum fold increase of the full length protein production over DMSO-treated samples as also determined by enzyme-linked immunosorbent assay within the concentration range tested (up to 1 mM).

TABLE 1

| Congener | $EC_{2X}$ (µM) | Max Fold over DMSO |
|---|---|---|
| Gentamicins | 500 | 3 |
| Compound 1 sulfate | 19 | 47 |
| Gentamicin A sulfate | 566 | 4.1 |
| Gentamicin C1 sulfate | 100 | 3.7 |
| Gentamicin C1a sulfate | 135 | 2.6 |
| Gentamicin C2 sulfate | 95 | 5.5 |
| Gentamicin C2a sulfate | 260 | 3.1 |

5.2 Typical Composition of the Gentamicin Complex

Table 2 shows the compositon of the gentamicin complex (see, Vydrin, A. F.; Shikhaleev, I. V.; Makhortov, V. L.; Shcherenko, N. N.; Kolchanova, N. V., Component Composition of Gentamicin Sulfate Preparations, Pharmaceutical Chemistry Journal (Translation of Khimiko-Farmatsevticheskii Zhurnal) (2003), 37(8), 448-450).

TABLE 2

| | Composition (%) | | | | | |
|---|---|---|---|---|---|---|
| Sample | A + Cpd 1 | B | C1 | C1a | C2a | C2 |
| 1 | 3 | 5 | 30 | 29 | 9 | 24 |
| 2 | 2 | 1 | 29 | 14 | 15 | 40 |
| 3 | 3 | 1 | 24 | 32 | 19 | 21 |
| 4 | 8 | — | 23 | 26 | 21 | 22 |
| 5 | 1 | 1 | 24 | 30 | 17 | 27 |
| 6 | 2 | 1 | 27 | 25 | 17 | 20 |

What is claimed is:

1. A method for treating a disease caused by premature translation termination, a nonsense mutation or a premature stop codon, for the purpose of minimizing the spread or worsening of said disease, comprising administering to a patient having said disease an effective amount of a compound having the structure of Compound 1:

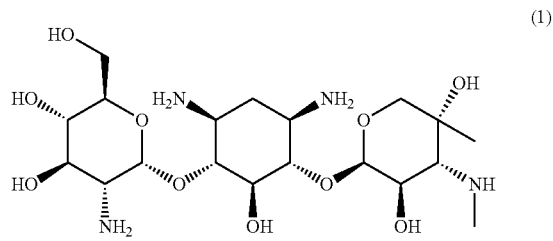 [SMILES: CN[C@@H]1[C@@H](O)[C@@H](O[C@@H]2[C@@H](O)[C@H](O[C@H]3O[C@H](CO)[C@@H](O)[C@H](O)[C@H]3N)[C@@H](N)C[C@H]2N)OC[C@]1(C)O]

(1)

having the name (2R,3S,4R,5R,6S)-5-amino-6-(((1R,2S,3S,4R,6S)-4,6-diamino-3-(((2R,3R,4R,5R)-3,5-dihydroxy-5-methyl-4-(methylamino)tetrahydro-2H-pyran-2-yl)oxy)-2-hydroxycyclohexyl)oxy)-2-(hydroxymethyl)tetrahydro-2H-pyran-3,4-diol, or a pharmaceutically acceptable salt or hydrate thereof; wherein, the compound is a purified stereoisomer.

2. The method of claim 1, wherein said disease caused by premature translation termination, a nonsense mutation or a premature stop codon is a germline or somatic nonsense mutation mediated disease selected from the group consisting of a nonsense mutation mediated cancer, an inborn error of metabolism, autoimmune disease, a blood disease, a collagen disease, diabetes, a neurodegenerative disease, a proliferative disease, a cardiovascular disease, a pulmonary disease, an ocular disease, a ciliopathy disease, an inflammatory disease, a central nervous system disease, a liver disease, a mucopolysaccharidosis disease, a kidney disease, a muscular dystrophy and a lysosomal storage disease.

3. The method of claim 2, wherein said autoimmune disease is selected from an immunodeficiency, rheumatoid arthritis or graft versus host disease; said blood disease is selected from hemophilia, Von Willebrand disease or beta-thalassemia; said disease is a diabetes selected from Type I diabetes or Type II diabetes; said neurodegenerative disease is ataxia-telangiectasia; said proliferative disease is tuberous sclerosis; said cardiovascular disease is selected from familial hypercholesterolemia or atherosclerosis; said inflammatory disease is arthritis; said central nervous system disease is-selected from multiple sclerosis, Alzheimer's disease, Tay Sachs disease, late infantile neuronal ceroid lipofuscinoses (LINCL) or Parkinson's disease; said lysosomal storage disease is tuberous sclerosis; said mucopolysaccharidosis disease is selected from Hurler syndrome, Hurler-Scheie syndrome, Scheie syndrome, Hunter syndrome, Sanfilippo syndrome A, Sanfilippo syndrome B, Sanfilippo syndrome C, Sanfilippo syndrome D, Morquio syndrome A, Morquio syndrome B, Maroteaux-Lamy syndrome A, Sly syndrome, Natowicz syndrome, metachromatic leukodystrophy, Niemann Pick's disease or Sandhoff disease; said kidney disease is selected from polycystic kidney disease or kidney stones; said collagen disease is selected from osteogenesis imperfecta, Marfan syndrome, or cirrhosis; said pulmonary disease is cystic fibrosis; said ocular disease is selected from aniridia, choroideremia, renal-coloboma syndrome, Lebers congenital amaurosis, retinitis pigmentosa, Bardet-Biedl syndrome, foveal hypoplasia, cataracts, Usher syndrome, Usher syndrome type 2A, central auditory processing difficulties, chorioretinal degeneration, congenital lens opacities, elevated intraocular pressure, exudative vascular retinopathy, glaucoma, iris hypoplasia, keratopathy, corneal degeneration, optic nerve hypoplasia, retinal detachment, secondary strabismus, tunica vasculosa lentis, Wilms tumor-aniridia-genital anomalies-retardation (WAGR) syndrome or Gillespie syndrome; said ciliopathy disease is selected from early embryonic death, hydrocephalus, polycystic liver disease or retinal degeneration; and said muscular dystrophy is selected from Becker or Duchenne muscular dystrophy.

4. The method of claim 1, wherein said patient is a human.

5. The method of claim 1, wherein said compound is administered as a pharmaceutical composition further comprising a suitable vehicle.

6. The method of claim 5, wherein said pharmaceutical composition is administered parenterally.

7. The method of claim 1, wherein said compound is administered in combination with an agent that inhibits the nonsense mediated mRNA decay pathway.

8. The method of claim 7, wherein said agent that inhibits the nonsense mediated mRNA decay pathway is selected from NMDI-1 or caffeine.

9. The method of claim 1, wherein said compound is administered in combination with an agent that suppresses premature termination codons to allow readthrough.

10. The method of claim 9, wherein said agent that suppresses premature termination codons to allow readthrough is selected from ataluren (PTC 124), another aminoglycoside, RTC13 or RTC14.

* * * * *